United States Patent
Eckerdal et al.

(10) Patent No.: US 7,248,927 B2
(45) Date of Patent: Jul. 24, 2007

(54) IMPLANTABLE HEART STIMULATOR WITH ELECTRODES FOR AN INFECTION CONTROL CURRENT

(75) Inventors: Johan Eckerdal, Bromma (SE); Martin Obel, Danderyd (SE); Eva Micski, Huddinge (SE)

(73) Assignee: St. Jude Medical AB, Jarfalla (SE)

( * ) Notice: Subject to any disclaimer, the term of this patent is extended or adjusted under 35 U.S.C. 154(b) by 501 days.

(21) Appl. No.: 10/468,587

(22) PCT Filed: Feb. 26, 2002

(86) PCT No.: PCT/SE02/00344

§ 371 (c)(1),
(2), (4) Date: Aug. 20, 2003

(87) PCT Pub. No.: WO02/068048

PCT Pub. Date: Sep. 6, 2002

(65) Prior Publication Data
US 2004/0098054 A1    May 20, 2004

(30) Foreign Application Priority Data
Feb. 27, 2001    (SE) .................................. 0100668

(51) Int. Cl.
*A61N 1/375* (2006.01)
(52) U.S. Cl. ............................... 607/36; 607/4; 607/37; 607/63
(58) Field of Classification Search ................ 607/4–5, 607/9, 37, 63, 36, 3
See application file for complete search history.

(56) References Cited

U.S. PATENT DOCUMENTS

| | | | |
|---|---|---|---|
| 4,886,505 A | | 12/1989 | Haynes et al. |
| 5,158,978 A | * | 10/1992 | Rubin .......................... 514/567 |
| 5,312,813 A | | 5/1994 | Costerton et al. |
| 5,409,467 A | | 4/1995 | Raad et al. |
| 5,462,644 A | | 10/1995 | Woodson |
| 5,713,926 A | * | 2/1998 | Hauser et al. .................. 607/5 |

(Continued)

OTHER PUBLICATIONS

"Prevention and Control of Bacterial Infections Associated with Medical Devices," Khoury et al., ASAIO Journal, 1992, pp. M174-M178.

(Continued)

*Primary Examiner*—George R. Evanisko
*Assistant Examiner*—Michael Kahelin
(74) *Attorney, Agent, or Firm*—Schiff Hardin LLP

(57) ABSTRACT

An implantable heart stimulator has an electrically conductive housing containing a pulse generator, with an electrode lead connected to the housing. The electrode lead has a proximal portion extending substantially from the housing to a location, after implantation, which is beyond the entry of the lead into the venous system and before the entry of the lead into the superior vena cava. A current source supplies an infection control current between the housing and an electrically conductive surface on the exterior of the proximal portion of the electrode lead, for counteracting bacterial growth. The housing may have a header to which the electrode lead is connected, in which case the header is provided with an electrically conductive surface as well, which can serve as an electrode for the infection control current.

29 Claims, 2 Drawing Sheets

U.S. PATENT DOCUMENTS 6,083,248 A * 7/2000 Thompson ............... 607/30
6,230,059 B1 * 5/2001 Duffin .................. 607/60
6,258,249 B1   7/2001 Simpson
6,282,444 B1   8/2001 Kroll et al.
6,295,474 B1 * 9/2001 Munshi ................. 607/121

OTHER PUBLICATIONS

"Mechanism of Electrical Enhancement of Efficacy of Antibiotics in Killing Biofilm Bacteria," Costerton et al., Antimicrobial Agents and Chemotherapy, Dec. 1994, pp. 2803-2909.

* cited by examiner

IMPLANTABLE HEART STIMULATOR WITH ELECTRODES FOR AN INFECTION CONTROL CURRENT

BACKGROUND OF THE INVENTION

1. Field of the Invention

The present invention relates to an infection control apparatus for an implantable heart stimulator of the type having a pulse generator for delivering electric stimulation pulses to a patient's heart through a lead connectable to the pulse generator, through a connector top on a pulse generator housing, the pulse generator housing being electrically conductive.

2. Description of the Prior Art

Implantable heart stimulator pocket infection is a severe complication which often ends up in explantation of the stimulator. The reason therefor is that conventional treatment with antibiotics cannot eradicate the infection. This seems to depend on the circumstance that the bacteria live in a biofilm formed around the exterior surfaces of the implanted stimulator, which film blocks antibiotics. The bacteria may also live passively on a very low metabolism and can therefore not be treated successfully by antibiotics.

A method of enhancing the effect of antibiotics by applying an electrical field across the bioflim is described in U.S. Pat. No. 5,312,813. This method is based on findings by J. W. Costerton et. al. Their studies have shown that the infection can be completely cured and no explantation has to take place by applying an electric field or a small current across the biofilm during antibiotic treatment, cf. also ASAIO Journal 1992, p. M174–M178, Khoury et. al, "Prevention and Control of Bacterial Infections Associated with Medical Devices", and Antimicrobial Agents and Chemotherapy, Vol. 38, No. 12, December 1994, p. 2803–2809, Costerton et. al., "Mechanism of Electrical Enhancement of Efficacy of Antibiotics in Killing Biofilm Bacteria". In these studies, generally, a low electric current of the order of 15–400 $\mu A/cm^2$ is applied onto the infected surface while immersed in a buffer with antibiotics. In the most successful studies a total killing of microorganisms was reported after only 8 hours of current and antibiotic treatment—tobramycin 2.5 mg/l, 15–400 $\mu A/cm^2$, during 8 h. This effect has been termed "the bioelectric effect".

These studies suggest that the electric field needs to be applied in close proximity to the infected implant. A possible explanation for the observed effect is that electrochemically generated products are needed for the bioelectric effect to occur. At the titanium surface, titanium being normally used in heart stimulator housings, the following electrochemical processes take place.

At the anode:

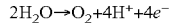   1)

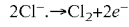   2)

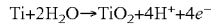   3)

At the cathode:

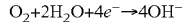   1)

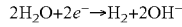   2)

It is supposed that primarily the produced oxygen and chloride gases have an influence on the biofilm attached to the surface. It is also supposed that the fact that the pH-value is lowered at the anode and increased at the cathode is significant for the influence and viability of the biofilm.

An infection that is initiated in the stimulator pocket will also often start to spread along the lead. The polymer surface of the lead may be a substrate for the bacteria and makes it easy for the bacteria to attach. At the time when a pocket infection is clinically manifested, in many cases the infection has already spread some distance from the stimulator pocket along the lead.

As the bioelectric effect is concentrated to parts in conjunction with or in close proximity to conducting surfaces of the implant, it is one purpose of the present invention to extend these conducting active surfaces.

SUMMARY OF THE INVENTION

The above object is achieved in accordance with the present invention in an implantable stimulator having a pulse generator with an electrically conductive housing, and an electrode lead connected to the pulse generator having a proximal portion which extends from the housing to a location, after implantation, situated between entry of the electrode lead into the venous system and before entry of the electrode lead into the superior vena cava, this proximal portion having an electrically conductive exterior surface, and a current source which supplies an infection control current between the metallic housing and the electrically conductive exterior surface of the proximal portion of the electrode lead.

The housing may be provided with a connector top or header, having a socket for making mechanical and electrical connection with the electrode lead, with at least a portion of the exterior surface of this connector top being electrically conductive. If a connector top of this type is present, at least two electrodes are formed from among the metallic housing, the electrically conductive portion of the exterior of the connector top, and the electrically conductive exterior surface of the proximal portion of the electrode lead, which are supplied with the infection control current by the current source.

As discussed above the bioelectric effect is limited to conducting surfaces of the implanted device or to the immediate proximity thereof. With the present invention a design is obtained which makes it possible to extend the bioelectric effect to surfaces of an implanted heart stimulator, which conventionally are non-conducting. The heart stimulation may be a pacemaker or a cardioverter-defibrillator (ICD). By making exterior surfaces of the proximal part of the lead and the connector top (if present) electrically conductive, all exterior stimulator surfaces located within the subcutaneous implant pocket and a part of the lead extending from the pocket are electrically conductive. By adapting these electrically conductive surfaces to form at least two separate electrodes and providing a current source to supply an electric infection control current between these electrodes, all exterior surfaces will be permeated by current, and the bioelectric effect will be extended to all surfaces within the pocket and also to the exterior surface of the proximal part of the lead. By making the normally non-conducting surfaces of the connector top and the lead electrically conducting, not only effective treatment of infections within the pocket is possible, but spreading of the infection from the pocket along the lead is prevented. The lead will in this way benefit from the bioelectric effect and thus bacteria are prevented from reaching the endocardium giving rise to endocarditis.

In an embodiment of the apparatus according to the invention an electrically conducting polymer is applied on said exterior surfaces of the proximal part of said lead and said possible connector top. In this way traditionally non-conducting surfaces of a heart stimulator are made electrically conductive. An example of a polymer suitable for this purpose is an electrically conducting polymer marketed under the trademark ELASTOSIL.

In another embodiment of the apparatus according to the invention an electrically conducting coil is applied around the proximal part of the lead. In this way the proximal part of the lead not only is made electrically conductive but also the wear resistance of the lead is improved.

In another embodiment of the apparatus according to the invention the exterior surfaces of the proximal part of the lead and of said connector top (if present) are treated by ion implantation technology or so-called Ion-Beam-Assisted-Deposition. This technique is especially well suited for making stimulator connector tops or headers of epoxy electrically conductive.

Other possible technologies to make a surface conducting are Physical Vapor Deposition, PVD, or Chemical Vapor Deposition, CVD or any sputtering process.

It has been found that oxide layers, especially titanium oxide layers but also other metal oxide layers may be formed when such metals are used in the DC current environment which exists in conjunction with the present invention. These oxide layers may cause an uneven current distribution possibly detrimental to the infection control effect. The current may also be lowered due to increased impedance caused by the oxide layer to a point at which the effect on bacteria in the biofilm is no longer effective. The formation of such oxide layers is avoided, according to an embodiment of the apparatus according to the invention, by coating the generator housing and other metallic surfaces that may become oxidized due to the DC current with one of the metals platinum, palladium or iridium or any other metal with similar electrochemical characteristics or an alloy of these metals.

In a further embodiment of the apparatus according to the invention the current source is formed by an electric pulse generator battery. Thus in case of heart stimulators, like pacemakers or ICDs, having their own energy source, no external source will be required.

In another embodiment of the apparatus according to the invention an inductive coupling arrangement provided to inductively couple an externally located current source to the electrodes thereby avoiding loading of the internal battery.

In a version of this embodiment of the apparatus according to the invention the inductive coupling arrangement is a single layer inductive coil attached to the outer surface of the pulse generator housing and electrically connected to the electrodes or an inductive coil positioned inside the pulse generator housing and electrically connected to the electrodes. Such single layer coils, which are manufactured preferably by screen printing, will not require much space and will consequently contribute to a compact stimulator construction. A rectifier is connected between the coil and one of the electrodes to supply a DC current to the electrodes. Such a coil might also be used as a telemetry coil.

In another embodiment the connector top and the pulse generator housing are adapted to be in mechanical contact with transcutaneously inserted needles that inject the infection control current from a current source located outside the patient's body.

The present invention also relates to a heart stimulator having a pulse generator for delivering electric stimulation pulses to a patient's heart through a lead, connectable to the pulse generator, through a connector top on a pulse generator housing, the pulse generator housing being electrically conductive, and having an infection control current generating apparatus as disclosed above.

DESCRIPTION OF THE PREFERRED EMBODIMENTS

Figure 1:
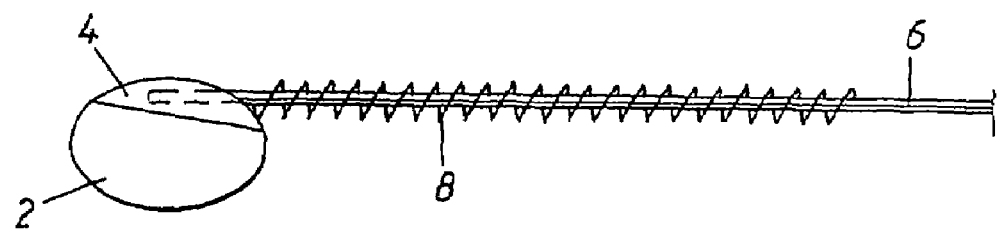
FIG. 1 is a schematic illustration of a heart stimulator with a lead provided with a coil at a proximal portion thereof, in accordance with the invention.

In the apparatus according to the invention, the proximal part of the lead, which extends to a position after implantation of the lead situated beyond the entry into the venous system and before the entry into the superior vena cava, is made electrically conductive. This can be realized in several different ways. Thus the proximal part can be made electrically conductive e.g. applying an electrically conducting polymer on its surface or by other techniques, previously described such as ion implantation technology, Ion-Beam-Assisted-Deposition (IBAD). In FIG. 1 another example of making a proximal lead part electrically conductive is shown.

FIG. 1 shows schematically an implantable heart stimulator 2 having a connector top 4 to which a lead 6 is connected. The proximal part of the lead 6 is made electrically conductive by wrapping a metallic coil 8 around this part of the lead. The metallic coil 8 will also improve the wear resistance of the lead 6.

The connector top or header 4 is often made of epoxy and IBAD or any of the previously described techniques is suitable for making such a connector top conductive.

Figure 2:
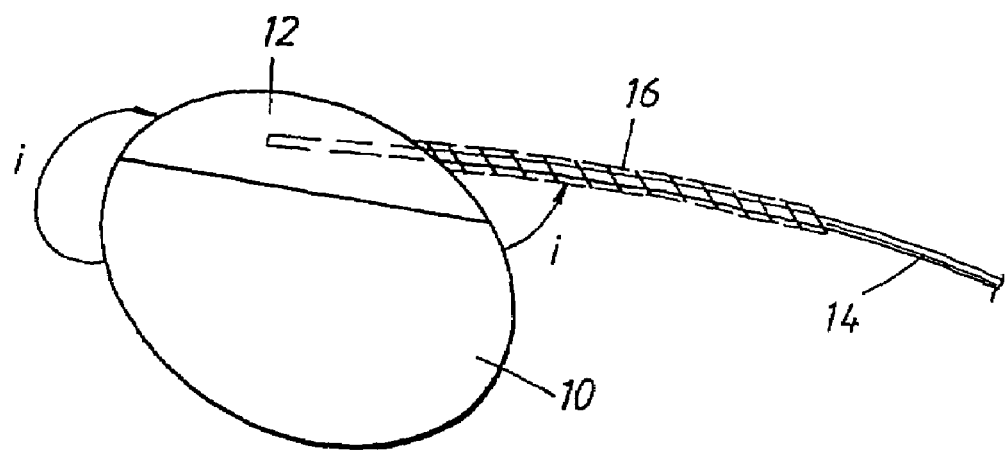
FIG. 2 is illustrates an embodiment of the invention with a pulse generator housing serving as a first electrode and at least one of the proximal portion of an electrode lead, and the connector top, serving as a second electrode, for the infection control current.

FIG. 2 shows an embodiment with an electrically conductive stimulator housing, an electrically conductive connector top 12 and a lead 14 with an electrically conductive proximal part 16. The pulse generator housing 10, which normally is made of titanium, serves as a first electrode and is isolated from the connector top 12 and the lead 14, which are forming a second electrode. The electrically conductive proximal part 16 of the lead 14 extends to a position which after implantation of the lead is situated beyond the entry into the venous system and before the entry into the superior vena cava. With this embodiment it is insured that all exterior surfaces of the implanted stimulator receive adequate therapy by connecting a current source (not shown in FIG. 2) in any suitable way to the electrodes.

The pulse generator housing, connector top and proximal part of the lead can be divided into two separate electrodes in a number of other ways. Thus, e.g. the pulse generator housing and connector top can form one electrode, while the proximal part of the lead forms the other. Other combinations are apparent. It is important, however, that the electrodes are designed such that the current distribution for the bioelectric effect is as uniform as possible across the exterior surfaces.

Figure 3:
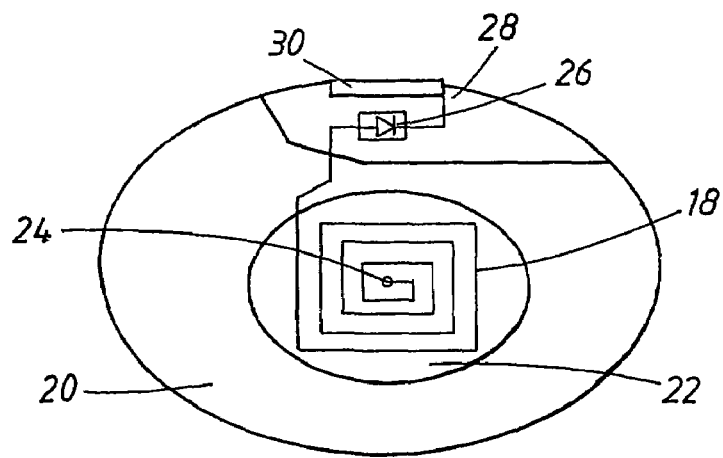
FIG. 3 is a schematic illustration of a heart stimulator in accordance with the invention with a surface mounted coil on the exterior of the stimulator housing for inductively connecting an external current source for the infection control current.

FIG. 3 shows schematically an embodiment for generating current for electric infection control by electromagnetic induction. Thus a super thin surface mounted coil 18 is attached to the exterior surface of the stimulator housing 20. This coil 18 can be manufactured by e.g. screen printing. A polymeric isolation film 22 is provided to electrically isolate the coil 18 from the stimulator housing 20.

One end 24 of the coil 18 is electrically connected to the housing 20, while the other end is connected to a diode 26 integrated in the epoxy connector head 28. The diode 26, in its turn, is connected to a counter electrode 30 at the external surface of the connector head 28.

By applying a high frequency electromagnetic field by an external energy source located in the proximity of the stimulator, a current will be generated in the coil 18. The diode 26 will allow current in only one direction and thus permit the electrochemical processes necessary for the bioelectric effect to occur. As an alternative, the coil can be placed inside the stimulator housing. One end of the coil is then connected to the stimulator housing, whereas the other end of the coil is connected via a diode to an external counter electrode, preferably integrated in the epoxy connector head.

Figure 4:
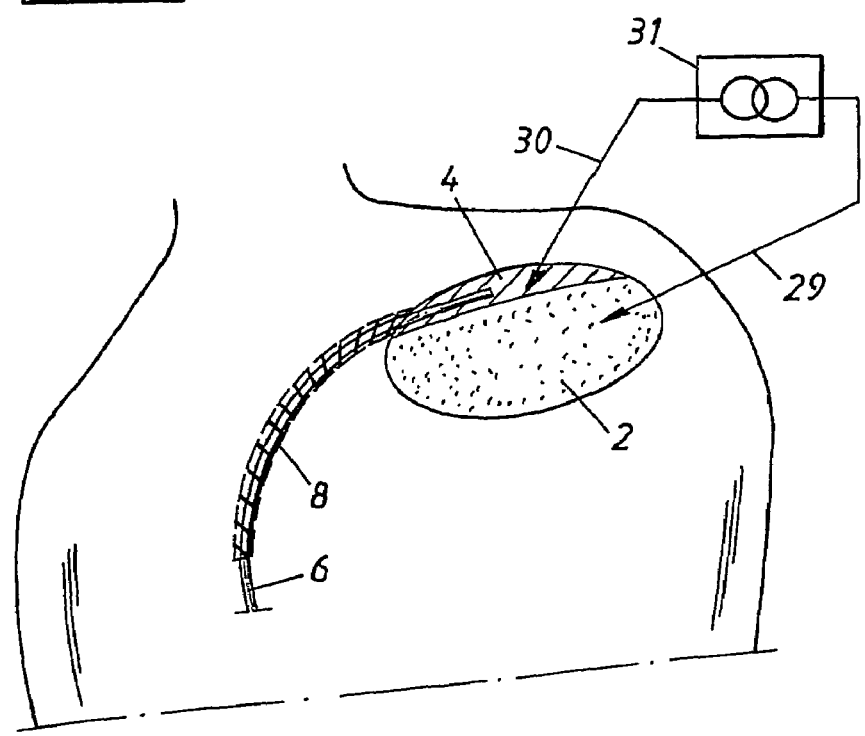
FIG. 4 illustrates an embodiment of the invention wherein the infection control current is delivered from an external current source via transcutaneous electrodes.

FIG. 4 shows schematically the implanted pulse generator in the patient. The conductive connector top 4 and the proximal conductive portion 8 of the lead 6 form one electrode and the casing 2 of the pulse generator form the other electrode. The external infection control current source 31 is connected to the conductive connector top and the pulse generator casing via transcutaneous electrodes 29,30

Although modifications and changes may be suggested by those skilled in the art, it is the invention of the inventors to embody within the patent warranted heron all changes and modifications as reasonably and properly come within the scope of their contribution to the art.

The invention claimed is:

1. An implantable heart stimulator comprising:
    a pulse generator and an electrode lead connected thereto for delivering electrical stimulation pulses to a heart of a patient, said pulse generator having an electrically conductive housing, said housing comprising a connector header in which said electrode lead is mechanically and electrically connected;
    said electrode lead having a proximal portion which, after implantation of said electrode lead, is configured to extend substantially from the housing to a location situated beyond entry of the electrode lead into the venous system and before entry of the electrode lead into the superior vena cava, said proximal portion having an exterior with an electrically conductive surface; and
    a current source for supplying an infection control current between said housing and said electrically conductive surface of said proximal portion of said electrode lead for counteracting bacterial growth at least on an exterior of said housing, said connector header having an exterior surface that is entirely electrically conductive and is in a flow path of said infection control current.

2. An implantable heart stimulator as claimed in claim 1 wherein at least one of said electrically conductive surface on the exterior of said proximal portion of said electrode lead and said electrically conductive surface on said exterior of said connector header is formed by an electrically conducting polymer.

3. An implantable heart stimulator as claimed in claim 1 wherein at least one of said electrically conductive surface on the exterior of said proximal portion of said electrode lead and said electrically conductive surface on said exterior of said connector header is formed by an ion implantation.

4. An implantable heart stimulator as claimed in claim 1 wherein at least one of said electrically conductive surface on the exterior of said proximal portion of said electrode lead and said electrically conductive surface on said exterior of said connector header is formed by ion beam assisted deposition.

5. An implantable heart stimulator as claimed in claim 1 wherein at least one of said electrically conductive surface on the exterior of said proximal portion of said electrode lead and said electrically conductive surface on said exterior of said connector header is formed by a coating process selected from the group consisting of vapor deposition and sputtering.

6. An implantable heart stimulator as claimed in claim 1 wherein said electrically conductive surface on said exterior of said connector header is electrically isolated from said electrically conductive surface on said exterior of said proximal portion of said electrode lead.

7. An implantable heart stimulator as claimed in claim 1 wherein said conductive surface at the exterior of said proximal portion of said electrode lead is formed by an electrically conductive coil.

8. An implantable heart stimulator as claimed in claim 1 wherein said housing has an exterior coated with a metal selected from the group consisting of platinum, palladium, indium, platinum alloys, palladium alloys and indium alloys.

9. An implantable heart stimulator as claimed in claim 1 wherein said electrically conductive surface at said exterior of said proximal portion of said electrode lead is electrically isolated from said housing.

10. An implantable heart stimulator as claimed in claim 1 wherein said current source comprises a battery contained in said housing, which also supplies power to said pulse generator.

11. An implantable heart stimulator comprising:
    a pulse generator and an electrode lead connected thereto for delivering electrical stimulation pulses to a heart of a patient, said pulse generator having an electrically conductive housing;
    said electrode lead having a proximal portion which, after implantation of said electrode lead, is configured to extend substantially from the housing to a location situated beyond entry of the electrode lead into the venous system and before entry of the electrode lead into the superior vena cava, said proximal portion having an exterior with an electrically conductive surface; and
    an extracorporeal current source, and an inductive coupling arrangement to inductively couple said extracorporeal current source with said housing and said electrically conductive surface on said exterior of said proximal portion of said electrode lead supplying an infection control current between said housing and said electrically conductive surface of said proximal portion of said electrode lead for counteracting bacterial growth at least on an exterior of said housing.

12. An implantable heart stimulator as claimed in claim 11 wherein said inductive coupling arrangement comprises a thin inductive coil attached at an outer surface of said housing, and electrically connected to said housing and to said electrically conductive surface on said exterior of said proximal portion of said electrode lead.

13. An implantable heart stimulator as claimed in claim 11 wherein said inductive coupling arrangement comprises a thin inductive coil disposed inside of said housing, and electrically connected to said housing and to said electrically conductive surface on said exterior of said proximal portion of said electrode lead.

14. An implantable heart stimulator as claimed in claim 11 wherein said inductive coupling arrangement includes a diode for producing a d.c. current as said infection control current.

15. An implantable heart stimulator as claimed in claim 11 wherein said inductive coupling arrangement includes transcutaneous electrodes connected between said extracorporeal current source and said housing and said electrically conductive surface on said exterior of said proximal portion of said electrode lead.

16. An implantable heart stimulator comprising:
a pulse generator which generates electrical stimulation pulses;
an electrically conductive housing containing said pulse generator and having a connector header;
an electrode lead mechanically and electrically connected in said header, and thereby connected to said pulse generator, for delivering said stimulation pulses to a heart of a patient;
said header having an exterior surface that is entirely electrically conductive;
said electrode lead having a proximal portion extending substantially from said housing to a location, after implantation of said electrode lead, adapted to be situated beyond entry into the venous system and before entry into the superior vena cava, said proximal portion having an exterior with an electrically conductive surface thereon;
a current source which supplies an infection control current in a flowpath including at least two of said housing, said electrically conductive surface on said exterior of said header and said electrically conductive surface on said exterior of said proximal portion of said electrode lead, to counteract bacterial growth at least one an exterior of said housing; and
at least one of said electrically conductive surface on the exterior of said proximal portion of said electrode lead and said exterior electrically conductive surface of said connector header being formed by an electrically conducting polymer.

17. An implantable heart stimulator as claimed in claim 16 wherein said conductive surface at the exterior of said proximal portion of said electrode lead is formed by an electrically conductive coil.

18. An implantable heart stimulator as claimed in claim 16 wherein said housing has an exterior coated with a metal selected from the group consisting of platinum, palladium, indium, platinum alloys, palladium alloys and indium alloys.

19. An implantable heart stimulator as claimed in claim 16 wherein said electrically conductive surface at said exterior of said proximal portion of said electrode lead is electrically isolated from said housing.

20. An implantable heart stimulator as claimed in claim 16 wherein said current source comprises a battery contained in said housing, which also supplies power to said pulse generator.

21. An implantable heart stimulator as claimed in claim 16 wherein said current source is an extracorporeal current source, and wherein said apparatus comprises an inductive coupling arrangement to inductively couple said extracorporeal current source with said housing and said electrically conductive surface on said exterior of said proximal portion of said electrode lead.

22. An implantable heart stimulator as claimed in claim 21 wherein said inductive coupling arrangement comprises a thin inductive coil attached at an outer surface of said housing, and electrically connected to said housing and to said electrically conductive surface on said exterior of said proximal portion of said electrode lead.

23. An implantable heart stimulator as claimed in claim 21 wherein said inductive coupling arrangement comprises a thin inductive coil disposed inside of said housing, and electrically connected to said housing and to said electrically conductive surface on said exterior of said proximal portion of said electrode lead.

24. An implantable heart stimulator as claimed in claim 21 wherein said inductive coupling arrangement includes a diode for producing a d.c. current as said infection control current.

25. An implantable heart stimulator as claimed in claim 21 wherein said inductive coupling arrangement includes transcutaneous electrodes connected between said extracorporeal current source and said housing and said electrically conductive surface on said exterior of said proximal portion of said electrode lead.

26. An implantable heart stimulator comprising:
a pulse generator which generates electrical stimulation pulses;
an electrically conductive housing containing said pulse generator and having a connector header;
an electrode lead mechanically and electrically connected in said header, and thereby connected to said pulse generator, for delivering said stimulation pulses to a heart of a patient;
said header having an exterior surface that is entirely electrically conductive surface;
said electrode lead having a proximal portion extending substantially from said housing to a location, after implantation of said electrode lead, adapted to be situated beyond entry into the venous system and before entry into the superior vena cava, said proximal portion having an exterior with an electrically conductive surface thereon;
a current source which supplies an infection control current in a flowpath including at least two of said housing, said electrically conductive surface on said exterior of said header and said electrically conductive surface on said exterior of said proximal portion of said electrode lead, to counteract bacterial growth at least one an exterior of said housing; and
at least one of said electrically conductive surface on the exterior of said proximal portion of said electrode lead and said exterior electrically conductive surface of said connector header being formed by an ion implantation.

27. An implantable heart stimulator comprising:
a pulse generator which generates electrical stimulation pulses;
an electrically conductive housing containing said pulse generator and having a connector header;
an electrode lead mechanically and electrically connected in said header, and thereby connected to said pulse generator, for delivering said stimulation pulses to a heart of a patient;
said header having an exterior surface that is entirely electrically conductive surface;
said electrode lead having a proximal portion extending substantially from said housing to a location, after implantation of said electrode lead, adapted to be situated beyond entry into the venous system and before entry into the superior vena cava, said proximal portion having an exterior with an electrically conductive surface thereon; and a current source which supplies an infection control current in a flowpath including at least two of said housing, said electrically conductive surface on said exterior of said header and said electrically conductive surface on said exterior of said proximal portion of said electrode lead, to counteract bacterial growth at least one an exterior of said housing; and at least one of said electrically conductive surface on the exterior of said proximal portion of said electrode lead and said exterior electrically conductive surface of said connector header being formed by ion beam assisted deposition.

28. An implantable heart stimulator comprising:

a pulse generator which generates electrical stimulation pulses;

an electrically conductive housing containing said pulse generator and having a connector header;

an electrode lead mechanically and electrically connected in said header, and thereby connected to said pulse generator, for delivering said stimulation pulses to a heart of a patient;

said header having an exterior surface that is entirely electrically conductive surface;

said electrode lead having a proximal portion extending substantially from said housing to a location, after implantation of said electrode lead, adapted to be situated beyond entry into the venous system and before entry into the superior vena cava, said proximal portion having an exterior with an electrically conductive surface thereon; and a current source which supplies an infection control current in a flowpath including at least two of said housing, said exterior electrically conductive surface of said header and said electrically conductive surface on said exterior of said proximal portion of said electrode lead, to counteract bacterial growth at least one an exterior of said housing; and at least one of said electrically conductive surface on the exterior of said proximal portion of said electrode lead and said exterior electrically conductive surface of said connector header being formed by a coating process selected from the group consisting of vapor deposition and sputtering.

29. An implantable heart stimulator comprising:

a pulse generator which generates electrical stimulation pulses;

an electrically conductive housing containing said pulse generator and having a connector header;

an electrode lead mechanically and electrically connected in said header, and thereby connected to said pulse generator, for delivering said stimulation pulses to a heart of a patient;

said header having an exterior surface that is entirely electrically conductive;

said electrode lead having a proximal portion extending substantially from said housing to a location, after implantation of said electrode lead, adapted to be situated beyond entry into the venous system and before entry into the superior vena cava, said proximal portion having an exterior with an electrically conductive surface thereon; and a current source which supplies an infection control current in a flowpath including at least two of said housing, said exterior electrically conductive surface of said header and said electrically conductive surface on said exterior of said proximal portion of said electrode lead, to counteract bacterial growth at least one an exterior of said housing; and said electrically conductive exterior surface of said connector header being electrically isolated from said electrically conductive surface on said exterior of said proximal portion of said electrode lead.

* * * * *